(12) United States Patent
Lecocq et al.

(10) Patent No.: US 12,201,125 B2
(45) Date of Patent: Jan. 21, 2025

(54) PEA PROTEIN COMPOSITION HAVING IMPROVED NUTRITIONAL QUALITY

(71) Applicant: ROQUETTE FRERES, Lestrem (FR)

(72) Inventors: Aline Lecocq, Mouvaux (FR); Mathias Ibert, La Chapelle d'Armentieres (FR)

(73) Assignee: Roquette Freres, Lestrem (FR)

( * ) Notice: Subject to any disclaimer, the term of this patent is extended or adjusted under 35 U.S.C. 154(b) by 32 days.

(21) Appl. No.: 16/652,569

(22) PCT Filed: Oct. 1, 2018

(86) PCT No.: PCT/FR2018/052403
§ 371 (c)(1),
(2) Date: Mar. 31, 2020

(87) PCT Pub. No.: WO2019/068998
PCT Pub. Date: Apr. 11, 2019

(65) Prior Publication Data
US 2020/0229462 A1 Jul. 23, 2020

(30) Foreign Application Priority Data
Oct. 4, 2017 (FR) .................................... 17 59287

(51) Int. Cl.
| | |
|---|---|
| *A23J 1/14* | (2006.01) |
| *A23J 3/14* | (2006.01) |
| *A23L 2/66* | (2006.01) |
| *A23L 11/30* | (2016.01) |
| *A23L 33/185* | (2016.01) |
| *A61K 36/48* | (2006.01) |

(52) U.S. Cl.
CPC . *A23J 1/14* (2013.01); *A23J 3/14* (2013.01); *A23L 2/66* (2013.01); *A23L 11/30* (2016.08); *A23L 33/185* (2016.08); *A61K 36/48* (2013.01)

(58) Field of Classification Search
CPC ..... A23J 1/14; A23J 3/14; A23L 11/30; A23L 33/185
See application file for complete search history.

(56) References Cited

U.S. PATENT DOCUMENTS

| | | |
|---|---|---|
| 7,186,807 B2 | 3/2007 | Salome et al. |
| 7,300,681 B2 | 11/2007 | Wasche et al. |
| 9,017,741 B2 | 4/2015 | Delbaere |
| 9,259,017 B2 | 2/2016 | Dhalleine et al. |
| 11,019,835 B2 | 6/2021 | Bourgeois et al. |
| 2008/0226810 A1* | 9/2008 | Passe .................. A23J 1/14 426/656 |
| 2010/0297333 A1 | 11/2010 | Kato et al. |
| 2015/0264971 A1 | 9/2015 | Saunders et al. |
| 2015/0368293 A1 | 12/2015 | Barata et al. |
| 2020/0230190 A1 | 7/2020 | Lecocq et al. |

FOREIGN PATENT DOCUMENTS

| | | |
|---|---|---|
| WO | 2006052003 A1 | 5/2006 |
| WO | 2012047252 A1 | 4/2012 |
| WO | 2018197822 A1 | 11/2018 |

OTHER PUBLICATIONS

Yang et al. (Evaluation of nutritional quality of a novel pea protein, AgroFOOD industry hi-tech—Nov./Dec. 2012—vol. 23 n 6, Retrieved from Internet URL: https://www.sprim.com/wp-content/uploads/2018/10/Evaluation-of-nutritional-quality-of-a-novel-pea-protein.pdf). (Year: 2012).*

Karaca et al., "Emulsifying properties of chickpea, faba bean, lentil and pea proteins produced by isoelectric precipitation and salt extraction", Food Research International, vol. 44, Issue 9, 2011, pp. 2742-2750, (https://doi.org/10.1016/j.foodres.2011.06.012.). (Year: 2011).*

The English translation of the International Search Report, mailed on Feb. 26, 2019, in the corresponding PCT Appl. No. PCT/FR2018/052403.

Anonyme: "Pea protein", Bulk Nutrients Sep. 15, 2015 (Sep. 15, 2015), XP002788006, Retrieved from the Internet: URL:https://www.bulknutrients.com.au/products/pea-protein.html[retrieved on Jan. 16, 2019] the whole document.

Reinkensmeier Annika et al: "Characterization of individual proteins in pea protein isolates and air classified samples", Food Research International, Elsevier, Amsterdam, NL, vol. 76, May 8, 2015 (May 8, 2015), pp. 160-167, XP029251386.

Anonyme: "Roquette NUTRALYS° plant-based proteins: Trusted, Competitive, Unique!", Roquette Jan. 25, 2017 (Jan. 25, 2017), XP002788026, Retrieved from the Internet: URL:https://www.roquette.com/food-and-nutrition/selected-ingredients/food-nutralys/ [retrieved on Jan. 16, 2019] the whole document.

Leterme P., Monmart T. and Baudart E.: "Amino acid composition of pea (*Pisumsativum*) proteins and protein profile of pea flour", Journal of the Science of Food and Agriculture, vol. 53, May 6, 1990 (May 6, 1990), pp. 107-110, XP002788010.

The Chilean Search Report, mailed on Jul. 23, 2021, in the related Chilean Appl. No. 202000897.

Wang et al: "Extrusion texturization of air-classified pea protein", Journal of Food Science, Wiley-Blackwell Publishing, Inc, US, vol. 64, No. 3, Jan. 1, 1999, pp. 509-513, XP002217135.

(Continued)

*Primary Examiner* — Stephanie A Cox

(57) ABSTRACT

The present invention relates to a pea protein composition the nutritional quality, and in particular the PDCAAS, of which is improved, as well as to a method for preparing same and to the use of this composition in a food or pharmaceutical composition.

8 Claims, No Drawings

(56) References Cited

OTHER PUBLICATIONS

The English translation of the Chinese search report, mailed on Sep. 1, 2022, in the related Chinese Appl. No. 201880064479.1.
Gao et al., "Pilot Scale Recovery of Proteins from a Pea Whey Discharge by Ultrafiltration," LWT—Food Science and Technology, vol. 34, Issue 3, May 2001, pp. 149-158.
Yang et al., "Rethinking plant protein extraction: Albumin—From side stream to an excellent foaming ingredient," Food Structure, vol. 31:100254, Jan. 13, 2022.
Mariotti et al., "The Influence of the Albumin Fraction on the Bioavailability and Postprandial Utilization of Pea Protein Given Selectively to Humans," J Nutr, 131(6):1706-13, Jun. 2001.

\* cited by examiner

PEA PROTEIN COMPOSITION HAVING IMPROVED NUTRITIONAL QUALITY

CROSS-REFERENCE TO RELATED APPLICATIONS

This application is a National Stage Application of PCT/FR2018/052403 filed Oct. 1, 2018, which claims priority from French Patent Application No. 17 59287, filed on Oct. 4, 2017. The priority of said PCT and French Patent Application are claimed. Each of the prior mentioned applications is hereby incorporated by reference herein in its entirety.

FIELD OF THE INVENTION

The subject of the present invention is a pea protein composition of which the nutritional quality, in particular its PDCAAS, is improved, the process for producing same and the use of this composition in a food or pharmaceutical composition.

PRIOR ART

Daily protein requirements are between 12% and 20% of food intake. These proteins are supplied both by products of animal origin (meat, fish, eggs, dairy products) and by plant foods (cereals, leguminous plants, algae).

However, in industrialized countries, protein intakes are predominantly in the form of proteins of animal origin. However, many studies demonstrate that excessive consumption of proteins of animal origin to the detriment of vegetable proteins is one of the causes of increase in cancers and cardiovascular diseases.

Moreover, animal proteins exhibit many disadvantages, both in terms of their allergenicity, regarding in particular proteins from milk or eggs, and in environmental terms, in connection with the damaging effects of intensive farming.

There thus exists a growing demand from manufacturers for proteins of plant origin having advantageous nutritional and functional properties without, however, exhibiting the disadvantages of compounds of animal origin.

Since the 1970s, the pea has been the leguminous seed plant that has been the most widely developed in Europe and mainly in France, particularly as a protein resource for animal feed but also for food for human consumption. The pea contains approximately 27% by weight of proteins. The term "pea" is considered here in its broadest sense and includes in particular all wild-type varieties of "smooth pea" and all mutant varieties of "smooth pea" and of "wrinkled pea", irrespective of the uses for which said varieties are generally intended (food for human consumption, animal feed and/or other uses).

Despite their undeniable qualities, pea proteins suffer from a nutritional power below animal and soy proteins. Indeed, several studies have shown that their PDCAAS is less than 1 (see for example "Aliments à base de soja—source de proteines de haute qualité [Soy-based foods—high quality source of protein]", ENSA, August 2015). The PDCAAS, or protein digestibility-corrected amino acid score, is used to assess the quality of proteins according to two criteria: essential amino acid requirements in human beings and protein digestibility. Since 1989, the WHO and the FAO have been advising the use of this method to determine protein quality. It is accepted that a protein that is nutritionally perfect must obtain in this method a score of 1 (or 100% depending on the expression of the result).

Many works and studies have tried to overcome this deficiency from which pea protein suffers. The PDCAAS of less than 1 is due at least in part to the presence of anti-nutritional factors co-extracted with the pea protein. Mention may be made, for example, of the antitryptic factors which, by inhibiting digestive trypsin, disturb the digestion of the protein. The applicant has therefore developed a process for producing a pea protein composition mainly comprising globulins and having a low content of anti-nutritional factors (see WO 2007/017572). The PDCAAS of this composition is clearly improved by reaching a value of 93% (or 0.93) (see "Vegetable Protein: A winner?", C. Lefranc-Millot, 2014). In order to reach the PDCAAS value of 1, a well-known solution consists in adding to this composition a mixture of proteins extracted from wheat (see further in "Vegetable Protein: A winner?", C. Lefranc-Millot, 2014). This elegant solution nevertheless has several disadvantages, such as the need to link together several steps in order to obtain the desired protein, and the use of wheat proteins which may contain traces of gluten.

Furthermore, while it is possible to envision obtaining a protein with a PDCAAS of 1 by mixing proteins other than pea, a mixture is obtained which loses the functional properties of said pea protein, in particular its emulsifying power. The preservation of an emulsifying power, while increasing its PDCAAS, so that it can easily be formulated in food recipes is a major requirement for certain industrial applications, in particular in the food, pharmaceutical and cosmetic fields.

There is therefore still an unmet need for a protein extracted only from pea, the nutritional quality of which is equivalent to those of animal proteins and the functional properties of which, in particular its emulsifying activity, remain high.

It is to the credit of the applicant company to have undertaken studies to meet these needs and to have developed the present invention. In particular, the applicant has developed a composition having a PDCAAS of 1 comprising only proteins extracted from pea by mixing the protein composition of application WO 2007/017572, the pea globulin fraction, with an albumin-rich pea extract. This solution would not have been contemplated by those skilled in the art because albumin-rich pea extracts also have a high content of antitryptic factors. Antitryptic factors are low-molecular-weight albumins, of 8 to 10 kDa, which are capable of irreversibly binding to the active sites of trypsin. They thus prevent the gastrointestinal hydrolysis of ingested proteins proteases and therefore reduce the digestibility of proteins and their PDCAAS. By succeeding in lowering the content of antitryptic factors in albumin-rich pea extracts and by combining them with globulin-rich pea extracts, the applicant has been able to obtain a pea protein composition having an excellent nutritional quality.

Furthermore, the mixing of the protein composition of application WO 2007/017572, the pea globulin fraction, with an albumin-rich pea extract, is carried out:
  by using an albumin-rich pea extract that is particular in that its emulsifying activity is greater than 600 ml of oil per gram of proteins, preferentially greater than 800 ml of oil per gram of proteins, even more preferentially greater than 1000 ml of oil per gram of proteins;
  and by carrying out this mixing by wet mixing, then drying the solution thus obtained, preferably by spray-drying.

DETAILED DESCRIPTION

A first subject of the present invention is a pea protein composition comprising globulins and albumins, characterized in that the solids extract of the composition:

comprises at least 80% by weight, preferably from 80 to 99% by weight, more preferentially from 85 to 98% by weight, from 90 to 97% by weight, from 92 to 95% by weight of proteins relative to the weight of the solids extract;

has a mass ratio of globulins to albumins from 65/35 to 85/15, preferably from 70/30 to 82/18, more preferentially from 75/25 to 80/20.

Preferably, the composition is characterized by an emulsifying activity greater than 300 ml of oil per gram of proteins, preferentially between 300 and 500 ml of oil per gram of proteins, preferentially between 350 and 450.

A second subject of the present invention is a process for producing a pea protein composition comprising the following steps:

a) extracting the globulins and albumins from pea in order to obtain a protein fraction;

b) separating the globulins from the albumins in order to obtain a globulin-enriched fraction and an albumin-enriched fraction;

c) reducing the content of antitryptic factors in the albumin-enriched fraction in order to obtain a treated albumin-enriched fraction;

d) adjusting the pH then heating the treated albumin-enriched fraction in order to obtain a thermized albumin-enriched fraction, the emulsifying activity of which is greater than 600 ml of oil per gram of proteins, preferentially greater than 800 ml of oil per gram of proteins, even more preferentially greater than 1000 ml of oil per gram of proteins;

e) mixing, in the presence of water, the globulin-enriched fraction and the thermized albumin-enriched fraction so that the solids extract of the mixture has a mass ratio of globulins to albumins from 65/35 to 85/15, preferably 70/30 to 82/18, more preferentially from 75/25 to 80/20;

f) drying the solution thus obtained.

Preferably, step d) is carried out by adjusting the pH between 6 and 8, preferentially between 6.5 and 7.5, and by heating between 130° C. and 150° C., preferentially 140° C., with a treatment time between 5 and 15 seconds, preferentially 10 seconds.

Preferably, step f) is carried out by spray-drying, preferentially by "multi-stage" spray drying.

A third subject of the present invention is the use of the pea protein composition according to the invention in a food or pharmaceutical composition.

The term "pea" should be understood in the present patent application as meaning all the wild varieties of "smooth pea" and all the mutant varieties of "smooth pea" and of "wrinkled pea".

The term "protein" should be understood in the present patent application as meaning macromolecules formed of one or more polypeptide chains consisting of the sequence of amino acid residues linked together by peptide bonds. In the specific context of pea proteins, the present invention relates more particularly to the globulins (approximately 50-60% by weight of pea proteins) and the albumins (20-25% by weight of pea proteins). Pea globulins are mainly subdivided into three subfamilies: legumins, vicilins and convicilins. Pea albumin is mainly subdivided into two families called PA1 and PA2.

The term "antitryptic factors" should be understood in the present application as meaning all of the compounds having an activity inhibiting digestive proteases, in particular trypsin. The method for calculating the content of antitryptic factors in the composition according to the invention is detailed in the examples of the present application.

The term "PDCAAS" should be understood in the present invention as meaning the Protein Digestibility-Corrected Amino Acid Score. This method is the one most commonly used today to estimate the protein quality of food intended for human consumption. The PDCAAS evaluates the quality of proteins according to two criteria: the essential amino acid requirements of human beings according to the FAO recommendations and the digestibility of proteins. Since 1989, the WHO and the FAO have been advising the use of this method to determine protein quality. It is accepted that a protein that is nutritionally perfect must obtain in this method a score of 1 (or 100% depending on the expression of the result). The method for calculating the PDCAAS of the composition according to the invention is detailed in the examples of the present application.

The term "emulsifying activity" should be understood to mean the maximum amount of oil that can be dispersed in an aqueous solution containing a defined amount of emulsifier before breaking or phase inversion of the emulsion (Sherman, P., 1995). A critique of some methods proposed for evaluating the emulsifying capacity and emulsion stabilizing performance of vegetable proteins. Ital. J. Food Sci., 1: 3). In order to quantify it, the applicant has developed a test that makes it possible to quantify it easily, quickly and reproducibly. This term is also well known under the terminology "Critical Micelle Concentration" or "CMC".

The various subjects of the invention will be better understood in the detailed description of the invention which follows.

The composition which is the subject of the present invention is a pea protein composition which comprises globulins and albumins.

In all that follows, the terms "proteins", "globulins" and "albumins" respectively denote proteins, globulins and albumins extracted only from pea. Thus, proteins, globulins and albumins extracted from a vegetable source other than pea or from an animal source are not encompassed by these terms. Globulins can be distinguished from albumins by various methods well known to those skilled in the art, in particular by their solubility in water, albumins being soluble in pure water, whereas globulins are only soluble in salt water. It is also possible to identify the albumins and globulins present in a mixture by electrophoresis or chromatography.

The solids extract of the composition according to the invention comprises at least 80% by weight, preferably from 80 to 99% by weight, more preferentially from 85 to 98% by weight, from 90 to 97% by weight, from 92 to 95% by weight, of proteins relative to the weight of the solids extract. Any reference assay method for quantifying the protein level well known to those skilled in the art can be used. Preferably, the total nitrogen is assayed (in %/crude) and the result is multiplied by the coefficient 6.25. This well-known methodology in the field of vegetable proteins is based on the observation that proteins contain an average of 16% nitrogen. Any method of assaying dry matter well known to those skilled in the art can also be used.

In addition, the solids extract of the composition according to the invention has a mass ratio of globulins to albumins from 65/35 to 85/15, preferably from 70/30 to 82/18, more preferentially from 75/25 to 80/20.

According to one particular embodiment, the albumins contained in the composition according to the invention essentially consist of albumins of the PA1 and PA2 type and lectins. Thus, the percentage by weight of the antitryptic factors relative to the weight of the proteins of the composition according to the invention is less than the percentage by weight of the antitryptic factors relative to the weight of the proteins in the pea in the natural state. Preferably, the solids extract of the composition according to the invention has a content of antitryptic factors of 1 to 5 TIU/mg. The content of antitryptic factors can in particular be measured according to the method described below.

The albumins of the composition according to the invention have an emulsifying activity greater than 600, preferably greater than 800, more preferentially greater than 1000 ml of corn oil per gram of albumins.

The emulsifying activity is defined as the maximum amount of oil that can be dispersed in an aqueous solution containing a defined amount of emulsifier before breaking or phase inversion of the emulsion (Sherman, 1995). In order to quantify it, the applicant has developed a test that makes it possible to quantify it easily, quickly and reproducibly. This process consists in carrying out the following steps:
 1. dispersion of 0.2 g of the product sample in 20 ml of water;
 1. homogenization of the solution with an Ultraturax IKA T25 device for 30 sec at a speed of 9500 revolutions per minute (rpm);
 3. addition of 20 ml of corn oil sold under the name Amphora by the company Cargill under homogenization under the same conditions as the preceding step 2;
 4. centrifugation for 5 minutes at 3100 g;
    at. if a good emulsion is obtained, the test is recommenced at step 1, increasing the amounts of water and corn oil by 50%;
    b. if a poor emulsion is obtained, for example a phase separation, the test is recommenced at step 1, reducing the amounts of water and corn oil by 50%.

The maximum amount of oil (Qmax in ml) that can be emulsified is thus determined iteratively.

The emulsifying activity is therefore the maximum amount of corn oil that can be emulsified per gram of product.

$$\text{Emulsifying activity}=(Q\max/0.2)\times 100$$

Albumins having an emulsifying activity greater than 600 ml of corn oil per gram of albumins can in particular be obtained by heating a protein fraction comprising albumins as described in step d) of the process below.

According to one particular embodiment, the composition according to the invention has a PDCAAS equal to 1 (or 100% depending on the expression of the results). Indeed, the low content of antitryptic factors in the composition according to the invention gives it good digestibility. The mass ratio of globulins to albumins in the composition according to the invention also contributes to a good amino acid balance. The presence of albumins makes it possible in particular to enrich the composition with sulfur-bearing amino acids. Thus, the composition according to the invention has excellent nutritional quality.

The composition according to the invention can in particular be obtained by the process for producing a pea protein composition described below.

The process for producing a pea protein composition which is the subject of the present invention comprises a step a) wherein the globulins and the albumins are extracted from pea in order to obtain a protein fraction.

According to one preferred embodiment, in step a) the globulins and the albumins are extracted from pea with a process comprising the following steps:

a-i) grinding the peas;
 a-ii) introducing the ground peas into an aqueous solution in order to obtain a solid phase A suspended in a liquid phase B; and
 a-iii) separating the liquid phase B, corresponding to the protein fraction, from the solid phase A.

Such a process is in particular described in patent application EP1400537.

The peas used in step a-i) may have previously undergone steps well known to those skilled in the art, such as in particular cleaning (removal of unwanted particles, such as stones, dead insects, soil residues, etc.) or even the removal of the external fibers of the pea (external cellulose hull) by a well-known step called "dehulling".

In step a-i), the peas can be ground in the absence of water (a process known as "dry grinding"). According to an alternative embodiment, the peas can be ground in the presence of water (a process known as "wet grinding"). In this case, step a-ii) is not implemented since a solid phase A is directly obtained in suspension in a liquid phase B at the end of the wet grinding step.

In step a-ii), the pH of the aqueous solution may in particular be between 6.2 and 7 and the temperature of the aqueous solution may in particular be between 5 and 20° C.

Step a-iii) makes it possible to separate the liquid phase B from the solid phase A. The liquid phase B corresponds to the protein fraction and is also called "soluble fraction". It contains proteins, in particular globulins and albumins, and also other compounds that are soluble in the aqueous phase, in particular salts, amino acids and carbohydrates. The solid phase A for its part contains the pea fibers and starch.

Preferably, the liquid phase B and the solid phase A are separated by fractionation. The separation by fractionation can in particular be carried out by means of centrifugal decanters or hydrocyclones.

The process according to the invention comprises a step b) wherein the globulins and the albumins are separated in order to obtain a globulin-enriched fraction and an albumin-enriched fraction.

The terms "globulin-enriched fraction" and "albumin-enriched fraction" are intended to mean a fraction having a percentage by weight of globulins, respectively of albumins, relative to the weight of proteins in said fraction, which is greater than the percentage by weight of globulins, respectively of albumins, relative to the weight of proteins in pea in its natural state. The enrichment therefore corresponds to the percentage increase in the proportion of globulins, respectively of albumins, between pea in its natural state and the enriched fraction. In particular, the enrichment of the enriched fraction is at least 5%, 10%, 15%, 20%, 25%, 30%, 35%, 40%, 45%, or 50% compared to pea in its natural state. The enrichment can in particular be obtained by purification and/or concentration of the protein fractions of interest in terms of globulins and albumins. These fractions, depending on the process applied, can be in hydrated or dry form.

Step b) can in particular be carried out by precipitation of the proteins at their isoelectric pH or by membrane separation, for example by ultrafiltration.

According to one preferred embodiment, in step b), the globulins are separated from the albumins with a process comprising the following steps:
 b-i) flocculating globulins of the protein fraction in order to obtain a solid phase C suspended in a liquid phase D; and
 b-ii) separating the liquid phase D, containing the albumins, from the solid phase C, containing the globulins.

Preferably, in step b-i), the flocculation of the globulins is carried out by bringing the pH of the protein fraction to the isoelectric pH of the globulins. More preferentially, the pH of the protein fraction is adjusted to 4.5. The flocculation of the proteins can in particular be carried out by heating the protein fraction at a temperature of 30 to 70° C., in particular for 5 to 30 minutes, more particularly between 10 and 30 minutes.

In step b-ii), the solid phase C (also called "floc") is preferably separated from the liquid phase D by centrifugation. The solid phase C corresponds to the globulin-enriched fraction and comprises the globulins. The liquid phase D corresponds to the albumin-enriched fraction and comprises the albumins and also other compounds that are soluble in the aqueous phase, in particular salts, amino acids and carbohydrates.

The process according to the invention comprises a step c) wherein the content of antitryptic factors in the albumin-enriched fraction is reduced in order to obtain a treated albumin-enriched fraction.

According to one preferred embodiment, in step c,) the treated albumin-enriched fraction has a content of antitryptic factors in the solids extract of 20 to 80 TIU/mg, preferably 30 to 50 TIU/mg.

Preferably, in step c), the content of antitryptic factors in the albumin-enriched fraction is reduced with a process comprising the following steps:
  c-i) carrying out a microfiltration or a centrifugation of the albumin-enriched fraction in order to obtain a microfiltration permeate or a centrifugation supernatant; and
  c-ii) carrying out an ultrafiltration of said microfiltration permeate or of said centrifugation supernatant in order to obtain an ultrafiltration retentate, corresponding to the treated albumin-enriched fraction.

The microfiltration of step c-i) results in a microfiltration permeate and a microfiltration retentate. It is the permeate which is then treated in the subsequent ultrafiltration step c-ii). The centrifugation of step c-i) results in turn in a centrifugation supernatant and a centrifugation sediment. It is the supernatant which is then treated in the subsequent ultrafiltration step c-ii).

When step c-i) is a microfiltration, it is preferentially a tangential membrane microfiltration. More particularly, the tangential microfiltration is preferentially carried out with a ceramic membrane having a porosity of from 0.01 µm to 1 µm, preferentially from 0.05 µm to 0.5 µm.

The ultrafiltration step c-ii) is carried out on the microfiltration permeate or on the centrifugation supernatant. It makes it possible to obtain, on the one hand, an albumin-rich ultrafiltration retentate and, on the other hand, a permeate rich in salts, amino acids and carbohydrates. More particularly, it is recommended to carry out the ultrafiltration using a membrane having a cut-off threshold of between 0.1 and 0.5 µm, the transmembrane pressure being kept below 4 bar.

The process according to the invention comprises a step d) wherein the treated albumin-enriched fraction is subjected to a pH adjustment and then to heating to obtain a thermized albumin-enriched fraction. This step makes it possible in particular to obtain albumins having an emulsifying activity greater than 600 ml of corn oil per gram of albumins.

According to one preferred embodiment, in step d), the pH of the treated albumin-enriched fraction is adjusted to a value between 6 and 8, preferably between 6.5 and 7.5. The pH of the treated albumin-enriched fraction can in particular be adjusted by adding a base chosen from sodium hydroxide, potassium hydroxide or aqueous ammonia, preferentially sodium hydroxide. It should be noted that the use of carbonate is to be avoided since it has a detrimental action on the taste of the albumin fraction obtained.

The heating of the treated albumin-enriched fraction after the pH adjustment can in particular be UHT heating, that is to say heating at a very high temperature for a short time. According to one preferred embodiment, in step d), the treated albumin-enriched fraction is heated at a temperature between 130° C. and 150° C., preferably 140° C., for a period of between 5 and 15 seconds, preferentially 10 seconds.

The process according to the invention comprises a step e) wherein the globulin-enriched fraction and the thermized albumin-enriched fraction are mixed so that the solids extract of the mixture has a mass ratio of globulins to albumins of from 65/35 to 85/15, preferably from 70/30 to 82/18, more preferentially from 75/25 to 80/20.

The globulin-enriched fraction and the thermized albumin-enriched fraction are mixed in a wet environment and said mixture is then dried. The mixing in a wet environment can in particular be carried out in any container suitable for this purpose, preferably equipped with an adequate stirring system, such as a movable shaft equipped with blades or turbines. After obtaining a homogeneous mixture, the latter is dried using techniques well known to those skilled in the art, such as spray-drying, preferentially "multi-stage" spray-drying, or else freeze-drying.

The process according to the invention can also comprise one or more optional steps before and/or after one of steps a) b) c), d) or e). According to one particular embodiment, the process according to the invention may comprise a step of enzymatic hydrolysis of the globulin-enriched protein fraction and/or of the treated albumin-enriched protein fraction, between step c) and step e). The type of enzyme used in the enzymatic hydrolysis reaction is preferably an enzyme of the protease group.

Without being bound by any theory, the applicant realized that it is the choice
  of an albumin-rich fraction that is particular in that its emulsifying activity is greater than 600 ml of oil per gram of proteins, preferentially greater than 800 ml of oil per gram of proteins, even more preferentially greater than 1000 ml of oil per gram of proteins
  then of its wet mixing with a globulin-rich fraction followed by drying of the solution thus obtained, preferentially by spray-drying
which makes it possible to obtain the unique properties of the composition which is the subject of the present invention.

A subject of the present invention is also the use of the pea protein composition according to the invention in a food or pharmaceutical composition.

Indeed, due to its excellent nutritional quality and low allergenicity, such a pea protein composition is of definite interest in many industrial applications, in particular in the food-processing or pharmaceutical industry, and in animal feed.

Food composition is understood to mean a composition intended for the feeding of human beings or animals. The term food composition encompasses foodstuffs and food supplements. Pharmaceutical composition is understood to mean a composition intended for a therapeutic use.

The examples which follow make it possible to better illustrate the application, without, however, limiting the scope thereof.

Example 1: Production of Pea Flour and Fractions Enriched Respectively with Pea Globulins and Pea Albumins Pea flour is initially prepared by grinding shelled fodder peas on an Alpine hammer mill equipped with a 100 µm grid. This flour will be called "pea flour".

300 kg of pea flour containing 87% by weight of dry matter are then soaked in water at the final concentration of 25% by weight of dry matter (DM), at a pH of 6.5. 1044 kg of flour suspension containing 25% by weight of DM (therefore 261 kg of dry flour) are then introduced with 500 kg of water into a hydrocyclone battery composed of 14 stages. It is fed with the flour suspension at stage No. 5. This separation leads to the obtaining of a light phase which corresponds to the output of stage No. 1. It consists of a mixture of proteins, fibers and soluble matter. This light phase at the hydrocyclone outlet contains as a mixture (142 kg of DM in total: fibers (approximately 14.8% by weight, i.e. 21 kg of DM), proteins (approximately 42.8% by weight, ie 60.8 kg of DM) and soluble matter (approximately 42.4% by weight, i.e. 60.2 kg of DM). This fraction has a DM content of 11.4% by weight. The fibers are separated on centrifugal decanters of Westfalia type used in an industrial potato starch processing unit. The light phase at the outlet of the centrifugal decanter contains a mixture of proteins and soluble matter, while the heavy phase contains the pea fibers. The heavy phase contains 105 kg of fibers at 20% by weight of DM. It is noted that virtually all of the fibers are indeed found in this fraction. As for the protein and soluble matter fraction, it contains 1142 kg of a mixture in solution of soluble matter and proteins (fraction containing 6% by weight of DM). The proteins are flocculated at their isoelectric point by adjusting the light phase at the outlet of the centrifugal decanter to a pH of 4.5 and heating at 50° C. The proteins thus flocculated are left for 10 minutes in a maturation tank. After precipitation of the proteins, centrifugal decanting is carried out, which makes it possible to recover sediment containing 56 kg of proteins (86% N×6.25 on a dry basis) containing 20% by weight of DM, and a supernatant containing, inter alia, the protein fraction containing the albumins. This sediment corresponds to the the protein fraction enriched with globulins and it will be referred to as "globulin-enriched fraction". The supernatant corresponds to the protein fraction enriched with albumins and it will be referred to as "albumin-enriched fraction".

The albumin-enriched fraction is then refined. Its pH is adjusted to 7.0 by adding 50% sodium hydroxide. The temperature of the suspension thus obtained was brought to 70° C. The solution is pumped through a microfiltration unit equipped with ceramic membranes of the Inside Ceram® type having a cut-off threshold of 0.14 µm (19 channels of 4.5 mm). Throughout the filtration, the temperature is regulated at 60° C. and the transmembrane pressure is maintained at a value between 0.4 and 0.6 bar. 707 liters of microfiltration permeate and 1768 liters of microfiltration retentate are thus recovered. 550 liters of the permeate are pumped through an ultrafiltration unit. The ultrafiltration unit is equipped with ceramic membranes of Kerasep® BX type sold by the company Novasep and having a cut-off threshold of 15 KDa (7 channels of 6 mm). Throughout the filtration, the temperature is regulated at 60° C. and the transmembrane pressure is maintained at a value between 1 and 3 bar. 467 liters of ultrafiltration permeate and 33 liters of retentate containing 75% by weight of proteins at 7.2% by weight of DM are thus recovered. This ultrafiltration retentate corresponds to the treated protein fraction enriched with albumins and will be referred to as "treated albumin-enriched fraction".

The pH of the treated albumin-enriched fraction is then adjusted, with stirring, to pH 6.8 by adding 50% concentrated sodium hydroxide. A UHT heat treatment is then applied by passing the treated albumin-enriched fraction over a Vomatec skid, at a temperature of 140° C. for a contact time of about ten seconds then by flashing under vacuum at approximately 90° C. The final product will be referred to as "thermized albumin-enriched fraction".

Example 2: Production of Pea Protein Compositions According to the Invention

A stainless steel tank fitted with a motorized stirrer is used. 1.89 kg of "globulin-enriched fraction" and 2 kg of "thermized albumin-enriched fraction" are introduced into this tank. This mixture makes it possible to obtain a ratio expressed as relative percentage of dry matter between the "globulin-enriched fraction" and the "thermized albumin-enriched fraction" of 75/25. The motorized agitator is then started and the product is homogenized for 15 to 30 minutes. The mixture is then sent to a single-stage spray-drying tower to be dried. A powder containing 95% by weight of DM is thus recovered. The product will be referred to as "75/25 pea protein composition".

The previous stainless steel tank fitted with a motorized stirrer is again used. 2.5 kg of "globulin-enriched fraction" and 2 kg of "thermized albumin-enriched fraction" are introduced into this tank. This mixture makes it possible to obtain a ratio expressed as relative percentage of dry matter between the "globulin-enriched fraction" and the "thermized albumin-enriched fraction" of 80/20. The motorized agitator is then started and the product is homogenized for 15 to 30 minutes. The mixture is then sent to a single-stage spray-drying tower to be dried. A powder containing 96% by weight of DM is thus recovered. The product will be referred to as "80/20 pea protein composition".

Example 2a: Production of Pea Protein Compositions Outside the Invention, Using "Treated Albumin-Enriched Fractions"

A stainless steel tank fitted with a motorized stirrer is used. 1.89 kg of "globulin-enriched fraction" and 2 kg of "treated albumin-enriched fraction" are introduced into this tank. As described above in example 2, this fraction is not neutralized at 6.8 and does not undergo UHT treatment. This mixture makes it possible to obtain a ratio expressed as relative percentage of dry matter between the "globulin-enriched fraction" and the "treated albumin-enriched fraction" of 75/25. The motorized agitator is then started and the product is homogenized for 15 to 30 minutes. The mixture is then sent to a single-stage spray-drying tower to be dried. A powder containing 95% by weight of DM is thus recovered. The product will be referred to as "75/25 pea protein composition".

Example 3: Methodology for Calculating Digestibility and PDCAAS

The measurement of the protein digestibility in rats is described in the following FAO article: "Protein Quality Evaluation. Report of a Joint FAO/WHO Expert Consultation. Rome, Italy."

For this, the experimental feed is composed of 10% by weight of the proteins to be tested, 1% by weight of an AIN93 vitamin mixture, 3.5% by weight of an AIN93 mineral mixture, 0.2% by weight of choline bitartrate, 5% by weight of cellulose, 10% by weight of corn oil. The feed is made up to 100% with corn starch.

This same feed not containing protein will be used as a control for the test. For this, the proteins will be replaced with corn starch.

Growing Sprague-Dawley rats (weight between 50 and 70 g at the start of the test) will be housed individually in metabolism cages at a temperature of between 18 and 24° C. and a humidity of between 40 and 70%. The rats will be fed a standard feed at least 2 days before the start of the test. They are then fed with the experimental diets for a minimum of 9 days consisting of a first period of acclimatization to the 4-day diets followed by a 5-day period of collecting feces. Water is given ad-libitum for the duration of the study. The feces thus collected daily are weighed, freeze-dried for 24 hours and ground. Measuring the nitrogen contained in the feed and in the feces will enable the protein digestibility to be calculated. The measurement method used is the Kjeldahl method.

The nitrogen ingested and the nitrogen excreted is obtained by multiplying the feed intake or the weight of the feces by the respective nitrogen levels. The basal nitrogen level is obtained by measuring the fecal nitrogen of animals fed the diet that does not contain protein.

The protein digestibility is obtained in the following way:

Digestibility=[Ingested nitrogen−(Fecal nitrogen−Basal nitrogen)]/Ingested nitrogen×100

The aminogram or total amino acid profile is established using the NF EN ISO13903: 2005 official method.

The amino acid score is determined as being the limiting essential amino acid with respect to the reference profile determined in adults. To obtain it, the following ratio must be calculated: [mg of the amino acid contained in 1 g of the test protein]/[mg of the amino acid of the reference profile]. The smallest value represents the amino acid score.

The PDCAAS (Protein digestibility-corrected amino acid score) is obtained by multiplying this limiting amino acid score by the protein digestibility determined in rats.

The reference profile in adults is described by FAO in its article: "Protein and amino acid requirements in human nutrition. Report of a joint WHO/FAO/UNU expert consultation". Geneva, Switzerland. 2007."

| Essential amino acid | g/g protein |
| --- | --- |
| Histidine | 15 |
| Isoleucine | 30 |
| Leucine | 59 |
| Lysine | 45 |
| Methionine | 16 |
| Cysteine | 6 |
| Methionine + Cysteine | 22 |
| Phenylalanine + Tyrosine | 30 |
| Threonine | 23 |
| Tryptophan | 6 |
| Valine | 39 |

Example 4: Methodology for Measuring the Content of Antitryptic Factors

The method for measuring the content of antitryptic factors consists in extracting the trypsin inhibitors with sodium hydroxide. Increasing volumes of the diluted sample are brought into contact with an excess of trypsin in the presence of N-alpha-benzoyl-DL-arginine p-nitroanilide (BAPNA) which will then be hydrolyzed in the form of p-nitroaniline, a compound which absorbs at 410 nm. After blocking of the reaction with acetic acid, the increase in coloration is measured with a spectrophotometer at 410 nm. The inhibitor content is then calculated from the rate of decrease in coloration. One unit of trypsin is arbitrarily defined as the amount of enzyme required to cause an increase of 0.01 unit of absorbance at 410 nm per 10 ml of reaction mixture under the conditions of the AOCS Ba 12-75 method. The antitryptic factor content is expressed in trypsin inhibition units per mg of sample to be tested (TIU/mg).

Example 5: Comparison of the Various Fractions

The table below summarizes the analyses of the PDCAAS (according to example 3), of the content of antitryptic factors (according to example 4) and of the emulsifying capacity (according to the method explained in the description).

| Reference | Content of antitryptic factors (TIU/mg) | Digestibility | PDCAAS | Emulsifying capacity (in ml of oil per g of proteins) |
| --- | --- | --- | --- | --- |
| Pea flour | Not done | 77.3 | 0.63 | |
| Globulin-enriched fraction | 3 | 97.3 | 0.93 | |
| Treated albumin-enriched fraction | 41 | 96.9 | 0.56 | 500 |
| Thermized albumin-enriched fraction | 9.8 | 97.1 | Not done | 1300 |
| 75/25 Pea protein composition according to the invention | 4 | 97.0 | 1 | 400 |
| 80/20 Pea protein composition according to the invention | 5 | 7.2 | 1 | 450 |
| pea protein compositions outside the invention, using "treated albumin-enriched fractions" | | | | 100 |

These examples clearly demonstrate the concentration of antitryptic factors in the albumin-enriched fraction, which therefore confirms the general teaching of the technical field indicating that these low-molecular-weight and hydro-soluble fractions are rich in antitryptic factors. Those skilled in the art would therefore have been dissuaded from reusing this fraction with the intention of improving the PDCAAS of the globulin-enriched fraction. They would instead have chosen to use complementary sources such as wheat proteins as taught in the prior art. The applicant has gone beyond this teaching and has developed a solution making it possible to obtain a protein of which the PDCAAS is equal to 1 based solely on protein fractions derived from pea.

Example 8: Production of a Drink of "Ready to Drink" Type

The various compositions are compared by virtue of their use in the drinks formulation referred to as "Ready To Drink". The various components are summarized in the following table:

| | 100% Milk control | Conventional isolate control | Invention 1 | Invention 2 | Outside the invention |
|---|---|---|---|---|---|
| water | | | | | 60 |
| Maltodextrin GLUCIDEX ® IT19 (ROQUETTE) | 18.74 | 18.34 | 18.51 | 18.51 | 18.51 |
| MPI Prodiet 85b milk protein | 10.8 | 5.53 | 5.53 | 5.53 | 5.53 |
| Nutralys S85F pea isolate | 0 | 5.67 | 0 | 0 | 0 |
| 75/25 Pea protein composition according to the invention | 0 | 0 | 5.5 | 0 | 0 |
| 80/20 Pea protein composition according to the invention | 0 | 0 | 0 | 5.5 | 0 |
| Pea protein compositions outside the invention, using "treated albumin-enriched fractions" | 0 | 0 | 0 | 0 | 5.5 |
| rapeseed oil | | | 3.78 | | |
| sucrose | | | 3.4 | | |
| sunflower oil | | | 2.52 | | |
| soy lecithin | | | 0.4 | | |
| vanilla flavoring | | | 0.36 | | |

The process for for producing drinks is the following:

Dry mixing of the powders (proteins, maltodextrins and sucrose),

Heating of the water to 50° C., addition of the powders, dispersion with a Silverson agitator for 30 min at 50° C., 3500 rpm, addition of vanilla flavoring, Mixing and separate melting of the soy lecithin and the oil at 50° C., After 30 min, addition of the lecithin/oil mixture to the aqueous solution, mixing with vigourous stirring for 5 min at 10 000 rpm, Heating at 75° C.

Two-step homogenization at 200 bar

Cooling and storage at 4° C.

In order to quantify the emulsion quality in the drinks, the particle size is measured using a Particle Size Analyser 3000 from the company Malvern. Dmode represents the mean size of the emulsified particles.

| in microns | 100% Milk control | Conventional isolate control | Invention 1 | Invention 2 | Outside the invention |
|---|---|---|---|---|---|
| D10 | 0.186 | 0.565 | 0.203 | | 3.61 |
| D50 | 0.546 | 43.1 | 0.482 | | 9.34 |
| D90 | 1.66 | 105 | 6.2 | | 103 |
| D mode | 0.577 | 69.1 | 0.444 | | 6.19 |
| D 4, 3 | 3.48 | 47.9 | 3.08 | | 35.1 |

Only the drinks produced with the invention make it possible to obtain particles that are as well emulsified as with the reference 100% milk control.

The invention claimed is:

1. A pea protein composition comprising dry matter comprising globulins and albumins, wherein the dry matter:
    comprises at least 80% by weight of proteins relative to the weight of the dry matter, wherein said proteins consist of pea proteins;
    has a mass ratio of globulins to albumins from 65/35 to 85/15; and
    has a content of antitryptic factors of 1 to 5 TIU/mg; and
    wherein the albumins have an emulsifying activity greater than 600 ml of corn oil per gram of albumins.

2. The composition as claimed in claim 1, having a PDCAAS equal to 1.

3. A process for producing a pea protein composition, comprising the steps of:
    a) extracting the globulins and albumins from pea in order to obtain a protein fraction;
    b) separating the globulins from the albumins in order to obtain a globulin-enriched fraction and an albumin-enriched fraction;
    c) reducing the content of antitryptic factors in the albumin-enriched fraction in order to obtain a treated albumin-enriched fraction;
    d) adjusting the pH then heating the treated albumin-enriched fraction in order to obtain a thermized albumin-enriched fraction; and
    e) mixing the globulin-enriched fraction and the thermized albumin-enriched fraction so that the solids extract of the mixture has a mass ratio of globulins to albumins from 65/35 to 85/15.

4. The process as claimed in claim 3, wherein, in step b), the globulins are separated from the albumins with a process comprising the following steps:
    b-i) flocculating globulins of the protein fraction in order to obtain a solid phase C suspended in a liquid phase D; and
    b-ii) separating the liquid phase D, containing the albumins, from the solid phase C, containing the globulins.

5. The process as claimed in claim 3, wherein, in step c,) the treated albumin-enriched fraction has a content of antitryptic factors in the solids extract of 20 to 80 TIU/mg.

6. The process as claimed in claim 3, wherein, in step d), the pH is adjusted to a value between 6.5 and 7.5.

7. The process as claimed in claim 3, wherein, in step d), the treated albumin-enriched fraction is heated at a temperature between 130° C. and 150° C., for a period of between 5 and 15 seconds.

8. A food or pharmaceutical composition, comprising the pea protein composition as defined in claim 1.

* * * * *